(12) United States Patent
Dogariu (10) Patent No.: US 7,821,620 B2
(45) Date of Patent: Oct. 26, 2010

(54) OPTICAL COAGULATION MONITOR AND METHOD OF USE

(75) Inventor: Aristide Dogariu, Winter Springs, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 592 days.

(21) Appl. No.: 11/906,644

(22) Filed: Oct. 3, 2007

(65) Prior Publication Data

US 2009/0091741 A1    Apr. 9, 2009

(51) Int. Cl.
*G01N 33/48* (2006.01)
(52) U.S. Cl. .................................. 356/39; 356/40
(58) Field of Classification Search ............. 356/39–40, 356/497, 477–482, 521; 436/177, 165, 909, 436/180; 250/227.19, 227.27; 435/13; 422/57–58, 422/68, 73, 81–82
See application file for complete search history.

(56) References Cited

U.S. PATENT DOCUMENTS

| 4,777,141 | A | 10/1988 | Calzi et al. |
| 5,039,617 | A | 8/1991 | McDonald et al. |
| 6,958,816 | B1 | 10/2005 | Dogariu et al. |
| 2007/0236698 | A1 | 10/2007 | Dogariu et al. |

*Primary Examiner*—Gregory J Toatley, Jr.
*Assistant Examiner*—Tri T Ton
(74) *Attorney, Agent, or Firm*—Thomas, Kayden, Horstemeyer & Risley, LLP (57) ABSTRACT

An optical coagulation monitor and the method of monitoring blood coagulation status are disclosed. The method includes positioning a sample probe containing an optical fiber within a circulating blood; transmitting a low-coherence light through the optical fiber into the blood; detecting dynamic light scatter signals generated by the blood within a coherence volume and received through the optical fiber; analyzing the dynamic light scatter signals in comparison to a predetermined coagulation criterion; and reporting the coagulation status of the blood. The method can be used for monitoring blood coagulation status in vivo or in vitro in real time. Further disclosed is a method of determining blood clotting time in vitro using the optical coagulation monitor.

25 Claims, 9 Drawing Sheets

OPTICAL COAGULATION MONITOR AND METHOD OF USE

FIELD OF THE INVENTION

The present invention relates to optical coagulation monitors based on low-coherence dynamic light scattering measurement for determining or monitoring blood coagulation status in vivo or in vitro in real time and for measurement of blood clotting time in vitro.

BACKGROUND OF THE INVENTION

Blood clotting is a complex process involving multiple initiators and cascades of activators which ultimately lead to the formation of fibrin and eventually to insoluble fibrin clots. The blood clotting process is an indicator of serious pathological conditions including thrombosis, pulmonary embolism, heart attack, stroke, and coronary artery disease which is the primary cause of mortality in the United States.

Conventionally, blood clotting process is assessed by measuring the time taken for a sample of blood to clot naturally or after a specific chemical coagulation initiator is introduced. The most commonly used tests for measuring the blood clotting time are the activated partial thromboplastin time (aPTT) test and prothrombin time (PT) test. The former is initiated by kaolin, PL (an emulsion of negatively charged phospholipids), and calcium; and the latter is initiated by thromboplastin and calcium. The conventional methods for determining the time of clot formations are typically based on mechanical, acoustical or electrical technologies. These methods are relatively slow and the instruments involved can be relatively bulky.

Optical measurements have been used in determining blood clotting time in vitro. U.S. Pat. No. 4,777,141 (to Calzi et al) discloses an instrument for measuring coagulation parameters, in which plasma and a reagent is mixed and a light scatter measurement is made on the mixture. The light scatter measurement is based on the transition of an initial homogenous liquid phase to a heterogeneous light-solid phase in which the threads of insoluble fibrin are formed.

U.S. Pat. No. 5,039,617 (McDonald et al) discloses a capillary flow device and the method for measuring activated partial thromoplastin time. This method performs an APTT analysis on a whole blood sample to which no anticoagulant has been added, by applying the sample to a capillary track, and by detecting the cessation of blood flow as determined by a light scatter measurement on blood cells passing through a specific location of the track.

On the other hand, U.S. Pat. No. 6,958,816 (to Dogariu et al) discloses methods and systems that use dynamic light scattering, for investigating local rheological responses of complex fluids over a frequency range larger than that provided by standard instrumentation.

Currently, no instrument is available for monitoring blood coagulation status in vivo in real time. It is known that patients who have undergone major surgery are at great risk of thrombosis up to 72 hrs after surgery. Under these conditions any significant increase in blood viscosity may most probably indicate the onset of thrombosis.

Therefore, there is a strong need for instrumentations and methodologies that enable early detection of clotting activation in real time, so that early therapeutic intervention can be started timely to avert thrombosis and death. Furthermore, there is further a strong need in the ability of monitoring the effectiveness of procoagulant or anticoagulant therapies in real time, which would allow the physicians to understand and control the therapeutic treatment. Moreover, it is also desirable to effectively monitor coagulation activities in vitro, and provide improved detection method for determining clotting time.

SUMMARY OF THE INVENTION

In one aspect, the present invention is directed to an optical coagulation monitor, which comprises a sample chamber including an inlet and an outlet connected to a circulation path; a light source providing a low-coherence light; a sample probe disposed within the sample chamber, the sample probe comprising an optical fiber optically connected to the light source for transmitting the low-coherence light into a blood sample contained in the sample chamber; an optical detector connected to the sample probe for detecting light signals received from the sample probe; and a dynamic light signal analyzer connected to the optical detector. The optical fiber can be a single-mode optical fiber or a multi-mode optical fiber.

In a further aspect, the present invention is directed to a method of determining or monitoring blood coagulation status. In one embodiment, the method comprises positioning a sample probe comprising an optical fiber within a circulating blood; transmitting a low-coherence light through the optical fiber into the blood; detecting dynamic light scatter signals generated by the blood within a coherence volume and received through the optical fiber; analyzing the dynamic light scatter signals in comparison to a predetermined coagulation criterion; and reporting a coagulation status of the blood. The monitoring blood coagulation status is in real time, and the circulating blood can be either in vivo or in vitro.

In one embodiment, analyzing the dynamic light scatter signals of the blood cells generates a power spectrum of intensity vs. frequency. The predetermined coagulation criterion can be a predetermined value or a range of one or more parameters obtained from the power spectrum; a shape or a rate of change in the shape of the power spectrum; a predetermined amount of change of storage modulus G', loss modulus G", or loss tangent tanδ. In another embodiment, analyzing the dynamic light scatter signals of the blood cells generates temporal autocorrelation of the dynamic light scatter signals. The predetermined coagulation criterion can be a predetermined value or a range of one or more parameters obtained from the temporal autocorrelation, or a predetermined amount of change in the shape of the temporal autocorrelation, or in the width of the temporal autocorrelation.

In a further aspect, the present invention is directed to a method of determining blood clotting time in vitro. In one embodiment, the method comprises mixing a coagulation initiator with a blood sample to form a sample mixture; transmitting a low-coherence light into the sample mixture; detecting dynamic light scatter signals generated by the sample mixture within a coherence volume; analyzing the light signals in comparison to a predetermined clotting criterion; and reporting the blood clotting time of the blood sample. The sample mixture is in a flowing or static condition during the detection.

DETAILED DESCRIPTION OF THE INVENTION

In one aspect, the present invention provides optical coagulation monitors for monitoring blood coagulation status in vivo or in vitro, or for measurement of blood clotting time in vitro.

Figure 1:
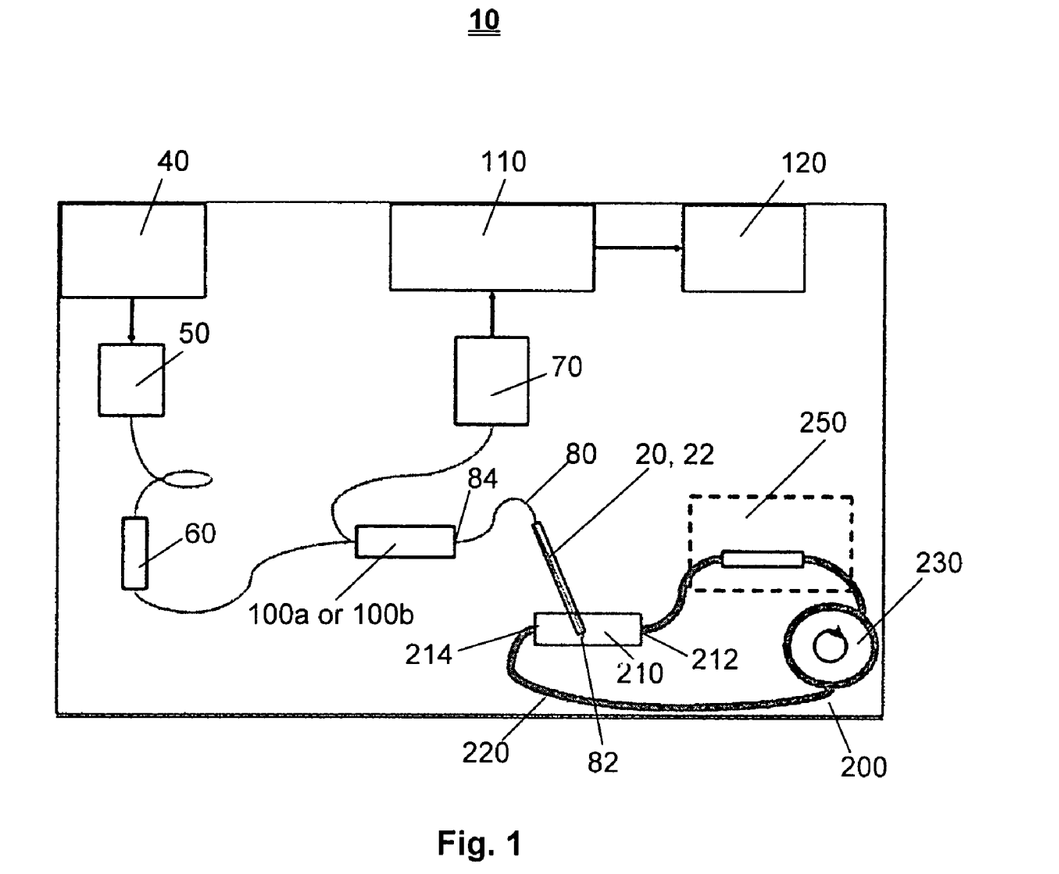
FIG. 1 is a schematic illustration of the optical coagulation monitor of one embodiment of the present invention.

In one embodiment, the optical coagulation monitor comprises a sample chamber connected to a circulation path, a low-coherence light source, a sample probe comprising optical fiber, an optical detector, and a dynamic light signal analyzer. FIG. 1 illustrates a schematic diagram of the optical coagulation monitor in one embodiment of the present invention. Herein, the term of dynamic light signal analyzer refers to a light signal analyzer that enables analysis of dynamic light signals. The term of dynamic light signals refers to time-dependent fluctuations observed when light is scattered by moving scattering centers such that the distance between them is constantly changing in time. Because of the constructive and destructive interferences in the scattered light, its intensity fluctuates in time and carries information about the movement of the scattering centers. This fluctuating intensity can be analyzed in either time or frequency domain.

More specifically, the optical coagulation monitor shown in FIG. 1 includes two major segments. The first segment includes the low-coherence light source and dynamic light scatter detection components, and the second segment includes a blood circulation system for conditioning blood sample for coagulation measurement in vitro.

Referring to FIG. 1, the blood circulation system 200 includes a sample chamber 210, which has an inlet 212 and an outlet 214, connected to a circulation path 220. In one exemplary embodiment, circulation path 220 is formed by a silicone tubing with its two opposing ends connected to inlet 212 and outlet 214. A pump 230 is connected to circulation path 220 for circulating the blood within circulation path 220. Typically, the blood to be measured is circulated at a low flow rate, for example, from about 0.05 to about 1.5 ml per minute. The interior surface of the circulation path is compatible to whole blood samples, which does not induce, or is resistant to, protein precipitation. Sample chamber 210 can further include a reagent inlet (not shown) for introducing a coagulation initiator.

Preferably, the temperature of the blood within the circulation path is controlled at about physiological temperature by a temperature control device (not shown). In one exemplary embodiment shown in Example 1, a water bath 250 is used to control the circulating blood at about 37° C. Other suitable temperature control device can also be used for the purpose of the present invention, for example, a semiconductor peltier.

Sample probe 20 comprises an optical fiber 80 which is also referred to as the sample branch of the optical detection system. Optical fiber 80 connects to fiber optic splitter 100 at its one end 84 and the opposing end 82, which is referred to as the sampling end hereinafter, is disposed within sample chamber 210 and immersed within the whole blood sample to be measured. Optical fiber 80 can be either a single-mode or a multi-mode optical fiber, as described in more detail below. In one exemplary embodiment, sample probe 20 includes a needle 22 with optical fiber 80 embedded within the needle, and with sampling end 82 of optical fiber 80 disposed at the end of needle 22 and exposing to the blood.

The light source 50 provides a low-coherence light. Preferably, the low-coherence light has a coherence length from about 5 μm to about 50 μm, and more preferably, from 8 μm to about 20 μm. Suitable low-coherence light source includes, but is not limited to, superluminescent diode (SLD), a multiple quantum well light emitting diode (MQWLED), a mod-elocked Ti:Al$_2$O$_3$ laser, a laser pumped fluorescent organic dye, and a superfluorescent optical fiber.

In an exemplary embodiment as illustrated in Example 1, a superluminescent diode (SLD) is used as the light source. In FIG. 1, the component 40 is a SLD current and temperature controller for the SLD light source.

The low-coherence light generated by light source 50 is transmitted by optical isolator 60 to sample probe 20. In one embodiment, optical isolator 60 is a fiber based. A fiber optic splitter 100a or a fiber optic coupler 100b connects to optical isolator 60 and optical detector 70 at one side and to optical fiber 80 of sample probe 20 at the other side. The fiber optic splitter or coupler directs the low-coherence light from light source 50 into optical fiber 80 of sample probe 20, and at the same time directs the light signals received from the sampling end 82 of optical fiber 80 to optical detector 70.

Optical detector 70 detects the light signals received from optical fiber 80 of sample probe 20. The light signals are converted by detector 70 to electrical signals, which are fed into a two-channel dynamic light signal analyzer 110. The two-channel dynamic light signal analyzer 110 can typically operate in the Fast Fourier Transform (FFT) mode with a base Frequency of 100 Hz and 800 FFT lines. The data generated by dynamic light signal analyzer 110 can be input to, through a general protocol interface board (GPIB) controller, and further processed by a personal computer 120.

In one embodiment, the optical coagulation monitor utilizes a single-mode optical fiber, which is also referred to as a single-mode optical coagulation monitor. Herein, the term "single-mode" optical fiber refers to an optical fiber having a narrow core diameter that only permits transmission of substantially one mode light signal. The term "multi-mode" optical fiber refers to an optical fiber having a broader core diameter that permits transmission of multiple modes of light signals. It is noted that the term "optical fiber" used herein includes gradient index and step index fibers, and specialty fibers such as photonic crystal fiber and structured fibers, etc.

In the single-mode optical coagulation monitor, both optical isolator 60 and optical fiber 80 of sample probe 20 are a single-mode optical fiber, and a fiber optic splitter 100a is used. For the low-coherence light used for the purpose of the present invention, the single-mode optical fiber can have a fiber core diameter from about 6 μm to about 8 μm. In one exemplary embodiment, a single-mode optical fiber having a wavelength of 630 nm, a fiber inner jacket of 125 µm, and a fiber core thickness of 8 µm is used. The terminators can be FC/PC.

Figure 2:
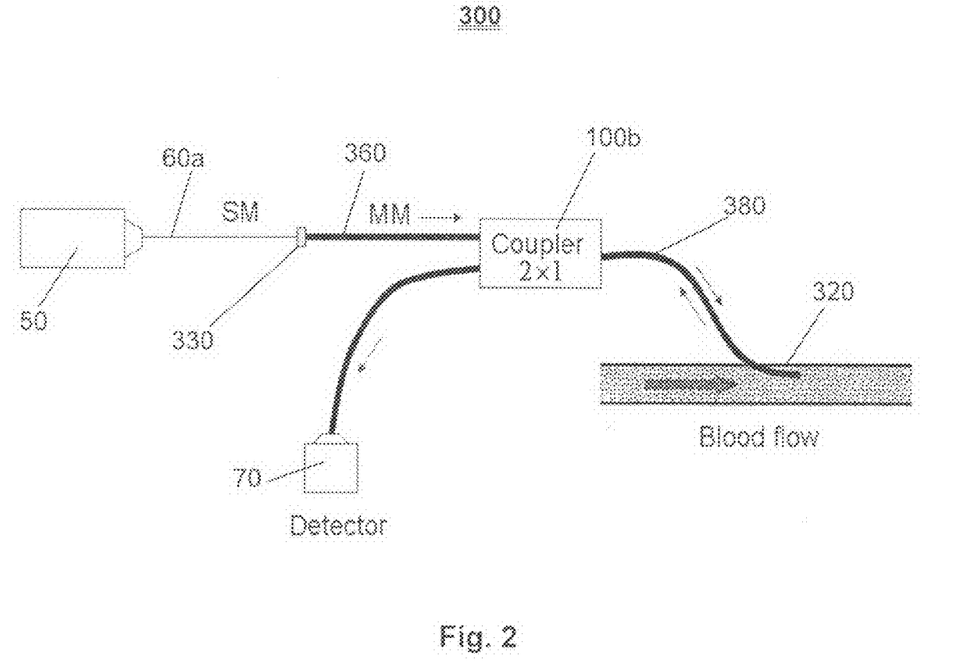
FIG. 2 illustrates a portion of a multi-mode optical coagulation monitor in one embodiment of the present invention.

In a further embodiment, the optical coagulation monitor utilizes a multi-mode optical fiber, which is referred to as a multi-mode optical coagulation monitor. Because the reference optical path is generated by reflection at the end of the fiber used to generate the measuring signal also, this interferometer is also referred to as multi-mode common path interferometer. In the multi-mode optical coagulation monitor, two figurations can be used. In one configuration, both optical isolator and optical fiber of sample probe are a multi-mode optical fiber, and a fiber optic coupler 110b is used In an alternative configuration as illustrated in FIG. 2, in the multi-mode optical coagulation monitor 300 a single-mode optical fiber 60a is connected to light source 50 at one end, and the other end is coupled to a multi-mode optical fiber 360 by a coupler 330. Multi-mode optical fiber 360 is in turn connected to fiber optic coupler 100b. For the low-coherence light used for the purpose of the present invention, the multi-mode optical fiber can have a fiber core diameter from about 40 µm to about 50 µm. In one exemplary embodiment, multi-mode optical fiber 60b and 380 have a wavelength of 630 nm, a fiber inner jacket of 125 µm thick, and a fiber core thickness of 50 µm. The single-mode optical fiber 60a coupled to multi-mode optical fiber 360 has a wavelength of 630 nm, a fiber inner jacket of 125 µm thick, and a fiber core thickness of 8 µm.

As can be further appreciated from the schematic illustration of FIG. 2, for monitoring coagulation status in vivo, sample probe 320 can be directly placed into a patient's blood circulation, such as alongside a central line (vein or artery). Therefore, the term "circulating blood" used herein includes naturally circulating blood in vivo, and a blood circulation generated in vitro, such as a blood sample contained in the blood circulation system 200 of FIG. 1.

Examples 1 and 2 illustrate specific examples of a single-mode optical coagulation monitor and a multi-mode optical coagulation monitor, respectively.

The principle and mechanism utilizing low-coherence dynamic light scattering and a single-mode optical fiber for analyzing mechanical properties of a small volume of liquid has been fully described in U.S. Pat. No. 6,958,816, which is hereby incorporated by reference in its entirety. Furthermore, the principle and mechanism utilizing low-coherence dynamic light scattering and a multi-mode, common-path interferometry for analyzing mechanical properties of a small volume of liquid has been fully described in patent application Ser. No. 11/399,632, which is hereby incorporated by reference in its entirety.

Figure 3:
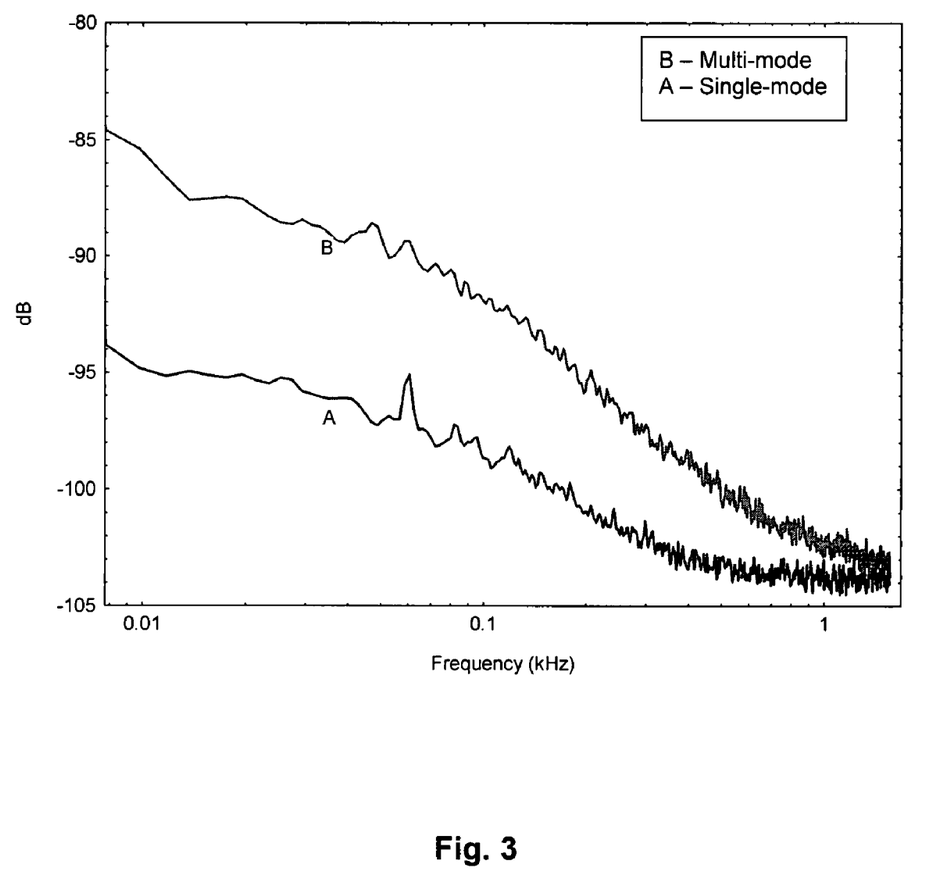
FIG. 3 shows the power spectra of a whole blood sample obtained using the optical coagulation monitors with a single-mode optical fiber and a multi-mode optical fiber, as described in Examples 1 and 2, respectively.

A whole blood sample is measured using the devices described in Examples 1 and 2, respectively. FIG. 3 shows the obtained power spectra. As shown, the power spectrum (intensity vs. frequency) obtained using the multi-mode optical fiber (curve B) has substantially higher intensity than the power spectrum obtained using the single-mode optical fiber (curve A). Additionally, different from the single-mode optical fiber, the power spectrum obtained using the multi-mode optical fiber does not flatten, which indicates that the multi-mode signal is not impacted by the noise floor, as is with the single-mode signal. Therefore, substantial improvements of signal amplitude and signal-to-noise ratio have been achieved in measuring whole blood samples using the multi-mode optical fiber in comparison to the single-mode optical fiber.

The method of using the instant optical coagulation monitors described above for coagulation measurement in vitro or monitoring blood coagulation status in vivo or in vitro are described hereinafter.

It should be understood that the instant method is based on measurement of the mechanical fluctuations of blood cells in whole blood. When irradiated, the blood cells scatter light in a random manner as determined by their mechanical movements. When the blood clotting progresses, the blood cell movement is affected and their limited displacement is detected via modifications in the fluctuations of the scattered light. The information regarding the clotting process, either being induced in vitro or naturally occurring in vivo such as thrombosis, is then inferred from the temporal autocorrelation of the light fluctuations or from the power spectrum, as described more fully hereinafter.

Since in blood the number of red blood cells is approximately two orders higher than the number of white blood cells, the dynamic light scatter signals of the blood cells are predominantly from the red blood cells. Other components in the blood, such as proteins in the plasma can also contribute to the dynamic light signals, however, to a substantially lower extent. Therefore, the signals from the red blood cells are the dominant components of the dynamic light scatter signals. It is noted that the detected light signals further include the reflected light signals at the interface between the sampling end of the optical fiber and the blood.

For the purpose of monitoring blood coagulation status or measurement of blood clotting time, it has been found that a low-coherence light having a frequency range from 600 nm to 700 nm can be used. Preferably, the coherence length is from about 5 µm to about 20 µm, more preferably, from about 8 µm to about 15 µm. The coherence volume is a volume of the blood immediately adjacent to the sampling end of the optical fiber, defined by the coherence length multiplied by the area of the fiber core. For example, when a multi-mode optical fiber having a fiber core diameter of 45 µm is used, with a coherence length of about 10 µm, about 15 fl of the blood sample is measured. Preferably, a multi-mode optical fiber is used to achieve higher detection sensitivity and higher signal-to-noise ratio.

In one embodiment, the blood clotting time is measured in vitro using the instant optical coagulation monitor. The method entails the following steps: mixing a coagulation initiator with a blood sample to form a sample mixture; transmitting a low-coherence light into the sample mixture; detecting dynamic light scatter signals generated by blood cells of the sample mixture within a coherence volume; analyzing the dynamic light signals in comparison to a predetermined clotting criterion; and reporting the blood clotting time of the blood sample.

Various coagulation initiators known in the art can be used for the purpose of the present invention. Suitable examples include, but are not limited to, elite, kaoline, glass cocktail, silica or phospholipids. Furthermore, the blood clotting time can also be measured without introducing coagulation initiator, i.e., natural clotting of the blood in vitro.

As described above, when the blood clotting progresses, the blood cell movement is affected and their limited displacement is detected via modifications in the fluctuations of the scattered light. The dynamic light scatter signals are predominantly from the red blood cells.

It is known, the shear stress σ in a flowing fluid represents the force exerted by the fluid per unit surface area of a plane parallel to the direction of flow and is given by $$\sigma = \eta \cdot \gamma \quad (1)$$

wherein η is the shear viscosity and γ is the shear rate. The shear stress σ(t) introduced by a small-amplitude deformation is sinusoidal and is defined as $$\sigma(t)=\gamma_0[G'(\omega)\sin(\omega t)+G''(\omega)\cos(\omega t)] \quad (2)$$

a regime known as the linear viscosity regime, where w is the angular frequency. The coefficient of the first term, G'(ω), in phase with the strain, is know as the storage modulus, and G''(ω), corresponding to the term in phase with the rate of strain, is known as the loss modulus. The former represents the storage of elastic energy by the fluid, the latter represents viscous dissipation. The ratio, known as the loss tangent, is defined as $$G''/G'=\tan\delta \quad (3)$$

and is a measure of the fluidity of the material; i.e., tan δ>>1 for liquid-like materials, while the opposite holds for solid-like materials. The storage and loss moduli collectively are a complex function G*, known as complex shear modulus, $$G^*=G'+iG'' \quad (4)$$

Wherein $i=(-1)^{1/2}$. The complex viscosity is then defined as $$\eta'-i\eta''=\eta^*=G^*/i\omega$$

The frequency-dependence of the storage and shear moduli provides information to the structure of complex materials. For liquid-like materials, one has $$G'<<G'' \quad (5)$$

and G' is proportional to $\omega^2$; G'' is proportional to ω, whereas for solid-like materials both are independent of frequency, but G'>>G''.

In one embodiment of the present invention, the measurable quantity is a power spectrum of the scattered light fluctuations P(ω). It has been found that in the high-frequency region, P(ω) is directly related to the power spectral density of the particle displacements $\langle\Delta r^2(\omega)\rangle$:

$$P(\omega) = \frac{\gamma q^2}{6}\langle\Delta r^2(\omega)\rangle. \quad (6)$$

The high-frequency dependence of the shear modulus G(ω) can be expressed by:

$$G(\omega) = \frac{1}{6\pi a}\frac{1}{\chi(\omega)}, \quad (7)$$

wherein α is the radius of the light scattering particles, and χ(ω) comprises two parts, the storage response χ'(ω) and loss response χ''(ω) that characterizes the fluid through $$\chi''(\omega) = \frac{\omega}{2k_BT}\cdot\langle\Delta r^2(\omega)\rangle, \quad (8)$$

and the storage χ'(ω) and loss response χ''(ω) are related through the Kramers-Kronig relationship:

$$\chi'(\omega) = \frac{2}{\pi}P\int_{-\infty}^{\infty}\chi''(\xi)\frac{\xi}{\xi^2-\omega^2}d\xi, \quad (9)$$

Thus, both G' and G'' can be extracted from the measured power spectrum of the blood sample.

As illustrated in FIG. 3, the obtained power spectrum is a two dimensional curve of intensity vs. frequency. Based on one or more of the spectral features, such as shape, slope, shear modulus G(ω) including the storage modulus G'(ω) and the loss modulus G''(ω), and other derived parameters, the predetermined clotting criterion can be determined using a known blood clotting time of a reference. In one example, the rate of change in the slope of a power spectrum is used as the predetermined clotting criterion. In another example, the storage modulus G'(ω), the loss modulus G''(ω), or the combination thereof is used as the predetermined clotting criterion.

It should be understood that all parameters described above, the power spectrum, G', G'', and tan δ, have a dependence on frequency ω. Therefore, the predetermined clotting criterion can be established in terms of the absolute value of one or more parameters in a narrow frequency range or via a global estimation over the entire spectral range available to the measurement.

It is further noted that the power spectrum is a result of measurement of the dynamic light scatter signals in frequency domain. Alternatively, the dynamic light scatter signals can also be measured in time domain. In other words, instead of analyzing the power spectrum one, can perform the entire analysis in the "time domain". More specifically, in the time domain measurement the dynamic light scatter signals from the detector are not fed into a power spectrum analyzer, instead, one evaluates the autocorrelation of the time series representing the detector output. This temporal autocorrelation has a simple Fourier transform relationship with the power spectrum. It should be understood that the information revealed from either the power spectrum or temporal autocorrelation is the same.

As such, in a further embodiment, the dynamic light scatter signals of a blood sample are recorded and the temporal autocorrelation is determined. The predetermined clotting criterion can be a predetermined value or a range of one or more parameters obtained from the temporal autocorrelation, such as one or more parameters defining the shape of the autocorrelation function from a reference, or a predetermined amount of change in the shape or width of the time autocorrelation.

It should be understood that for measuring blood clotting time in vitro, not only the sample probe 20 or 120 comprising an optical fiber as described above can be used for the measurement, an open system as those illustrated in FIGS. 10 and 11 of U.S. Pat. No. 6,958,816 can also be used. Furthermore, in this embodiment the sample mixture can be either in a circulating or a static condition. In the latter case, the sample mixture can also be simply placed in a sample well, allowing placement of the sampling end of the optical fiber within the well or configured to receive the incident light from the open system.

The red blood cell concentration in the normal peripheral blood is from about 4.2 to $5.9\times10^{12}$ cells per liter. Hematocrit (Hct) is defined as the proportion of blood volume that is occupied by red blood cells. The normal hematocrit range for male is from about 45% to about 52%, and for female is from about 37% to about 48%. As described above, the dynamic light scatter signals are predominantly from the red blood cells, the dependency of the dynamic light scatter signals on the red blood cell concentration of a sample has been assessed.

As shown in Example 3, the sensitivity of the power spectrum to the hematocrit (Hct) level was measured using the multi-mode optical coagulation monitor described in Example 2. Reconstructed anti-coagulated whole blood samples with different hematocrit were used for the measurement. More specifically, a series of whole blood samples with increasing amounts of red blood cells from plasma only, Hct of 30%, 35%, 40%, 45%, and 50% are measured. Among these reconstructed whole blood samples, the samples having Hct of 40%, 45%, and 50% are within the clinical normal range.

Figure 4:
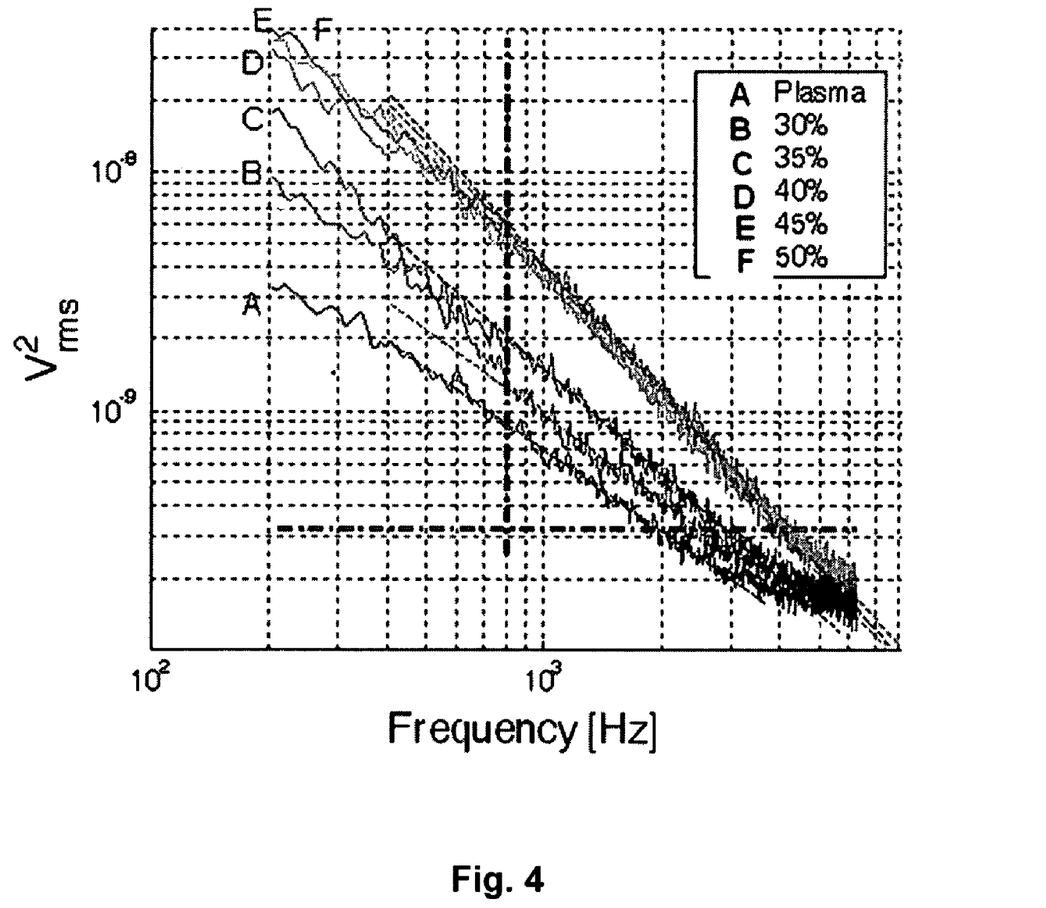
FIG. 4 shows the power spectra of the reconstructed whole blood samples with different levels of hematocrit, as described in Example 3.

FIG. 4 displays the obtained power spectra, which shows the dependency of the power spectrum on the hematocrit of the whole blood samples in the hematocrit range tested. However, within the clinical normal hematocrit range, the power spectra are essentially independent of the hematocrit of the blood samples.

Table 1 shows the parameter $\alpha$ obtained by linear fitting of the power spectrum measured at high frequencies, which is indicative of the type of diffusion regime. A strong dependence of $\alpha$ on the hematocrit has been observed. This observation indicates a tendency towards normal diffusion ($\alpha=1$), when the hematocrit increases. Since the intensity of the signal obtained for plasma only is much lower than the intensity of the sample having 40% Hct, it can be concluded that for the whole blood samples having hematocrit within the clinical normal range, the heterodyne signal is mainly due to the motion of the red blood cells.

Figure 5:
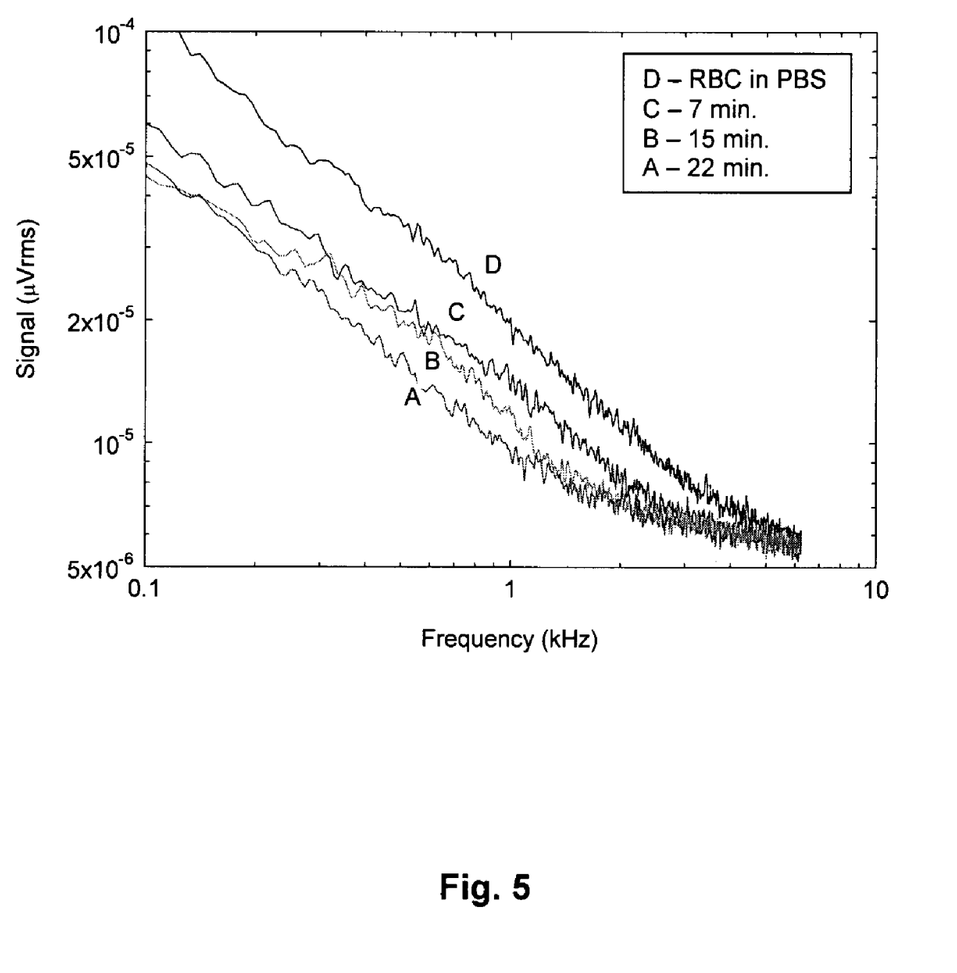
FIG. 5 shows the power spectra of a blood sample obtained at different time after addition of thrombin, as described in Example 4.

Example 4 illustrates the measurement of dynamic viscosity change during thrombosis of a whole blood sample using the multi-mode optical coagulation monitor described in Example 2. As shown, after introducing thrombin into the whole blood sample, coagulation occurred as indicated by the change of the power spectrum with time due to increase in viscosity. After 22 minutes, a clot formed in front of the optical fiber, and no further change was noted in the spectrum afterwards. FIG. 5 shows the obtained power spectra of the blood sample at 7, 15 and 22 minutes. Moreover, FIG. 5 further shows the power spectrum of washed red blood cells suspended in PBS, which represents the minimum viscosity obtainable using erythrocytes suspended in a medium with a viscosity close to water.

The results show that the instant optical coagulation monitor can detect both reduction and increase in viscosity of the blood samples. In the case of increased viscosity due to blood coagulation, sequential increases are observed to the point of gel formation due to clotting.

This result demonstrates that the process of blood clotting can be dynamically tracked over a period of time by measurement of increasing viscosity. This is particularly relevant in the context of early detection of onset of thrombosis in clinical settings such as in intensive care units. Patients who have undergone major surgery are at great risk of thrombosis up to 72 hours after surgery. Under these conditions any significant increase in blood viscosity may most probably indicate the onset of thrombosis. Using the instant optical coagulation monitor in vivo such as in the patient's circulation (possibly alongside a central line or canula), as described in the further embodiment of the present invention hereinafter, could provide early detection of clotting activation, therefore, therapeutic intervention could be started to avert overt thrombosis and death.

Figure 6:
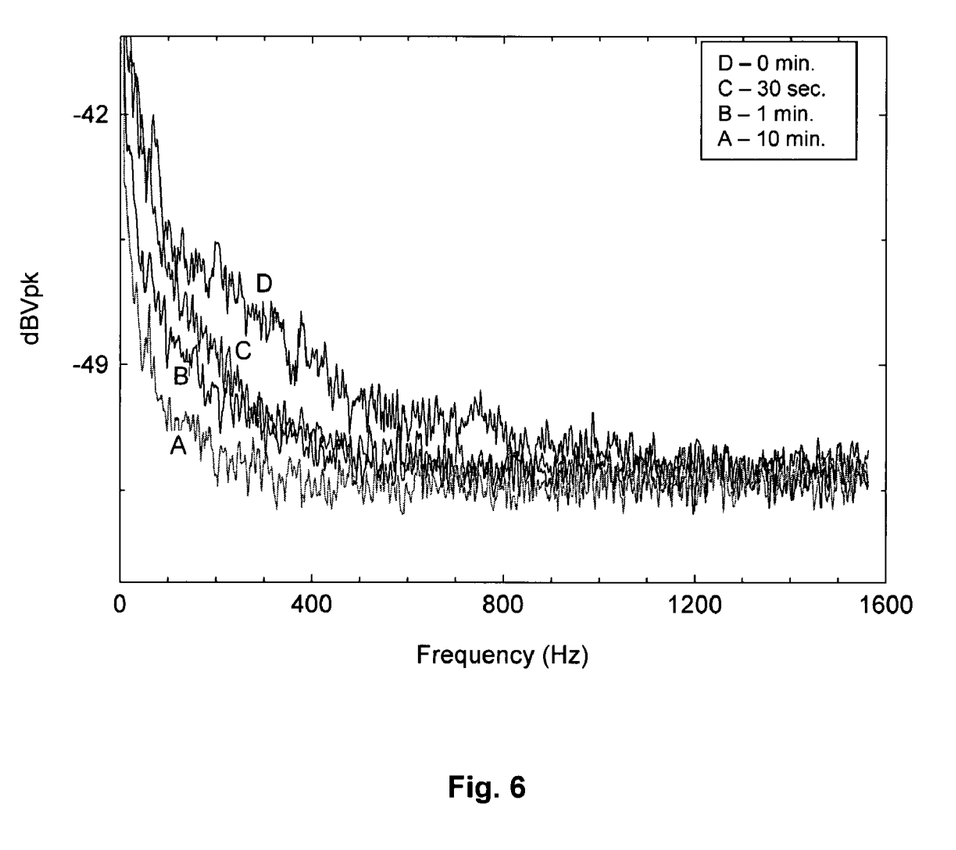
FIG. 6 shows the power spectra of a blood sample obtained at different time after addition of thrombin, as described in Example 5.

Example 5 further illustrates a specific method using the change in the shape of the power spectra with time for measurement of blood clotting time of whole blood samples. As shown, after introducing thrombin into a whole blood sample, blood coagulation occurred within about 5 to 7 minutes, and an increase in viscosity was observed over time as illustrated in FIG. 6. Sequential increases of the blood viscosity were observed to the point of gel formation due to clotting.

Figure 7:
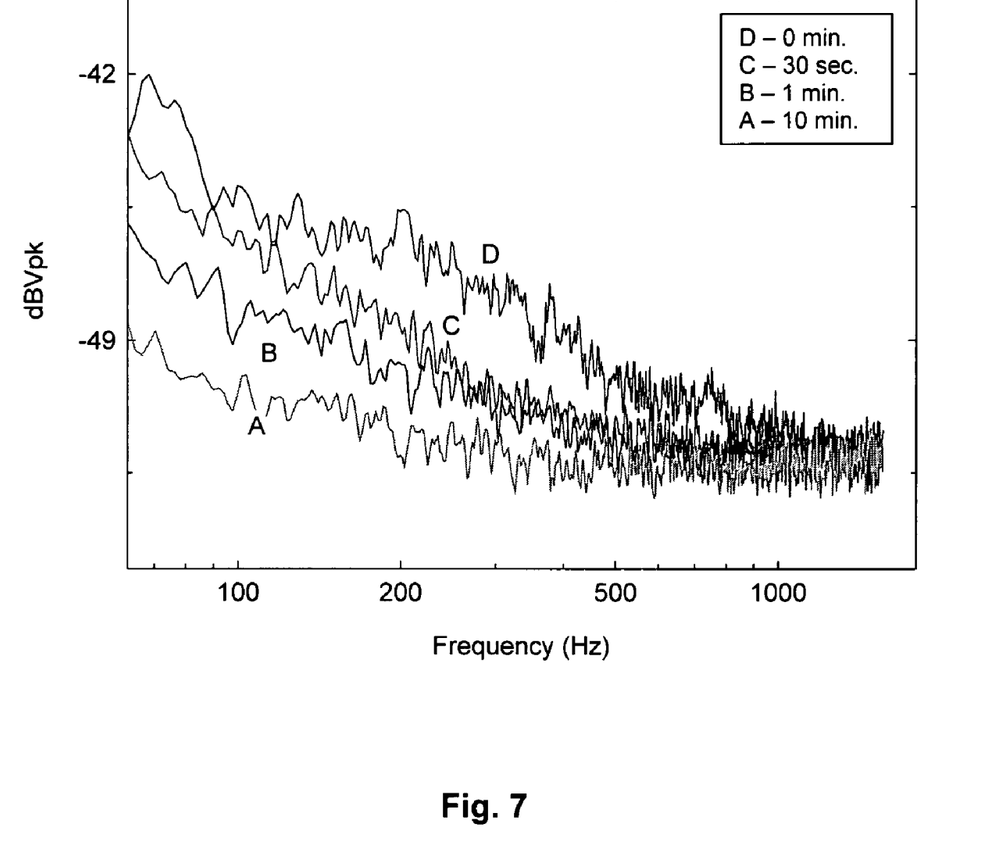
FIG. 7 is a log-log representation of FIG. 6, showing the changes in the slope of the power spectra, as described in Example 5.

FIG. 6 shows an expanded region of the collected power spectra, and a significant decrease in the bandwidth is observed. It has been found that the actual changes in the viscosity properties are best demonstrated by the changes in the shape of the power spectra. FIG. 7 is a log-log representation of the power spectra shown in FIG. 6. As can be readily appreciated from FIG. 7, the slope of the power spectrum changes significantly as the aggregation process evolves. Quantitative determination of the viscoelastic properties can be made based on these changes of the spectra. It is noted that when the change in the slope of the spectrum is used as the parameter for determining the blood clotting time, the measurement is independent of the absolute value of the initial viscosity of a blood sample. This result illustrates that the optical coagulation monitor and the method of the present invention can be used for a quantitative measurement of blood clotting time.

It is known that the two major proteins in blood are albumin (normal range 60-80 mg/ml) and fibrinogen (normally about 3 mg/ml). Albumin is primarily responsible for the viscosity of blood, and it is important in regulating osmotic pressure and water retention in the circulation. Fibrinogen concentration gradually increases with age to concentrations of 6 mg/ml or more in both males and females, therefore, it is a risk factor for cardiovascular disease.

The sensitivity of the instant optical coagulation monitor to the difference in fibrinogen and albumin concentrations, and the viscosity change affected by the proteins has also been assessed. Example 6 illustrates two specific examples.

In the first example, washed red blood cells were suspended in PBS with a hematocrit of 45%, and in PBS solutions that contained 1.3 and 5.5 mg/ml of fibrinogen, respectively. As described above, the washed red blood cells suspended in PBS alone represent the minimum viscosity detectable using erythrocytes as the viscosity reporters, since the viscosity of PBS is close to that of water, and significantly less than that of plasma. The power spectra of these three suspensions were obtained using the multi-mode optical coagulation monitor described in Example 2. As shown, the viscosity increased with the concentration of fibrinogen. Moreover, the increase in viscosity observed at a fibrinogen concentration of 1.3 mg/ml indicated that the multi-mode optical coagulation monitor of the present invention was sufficiently sensitive to detect small changes in fibrinogen concentration.

Figure 9:
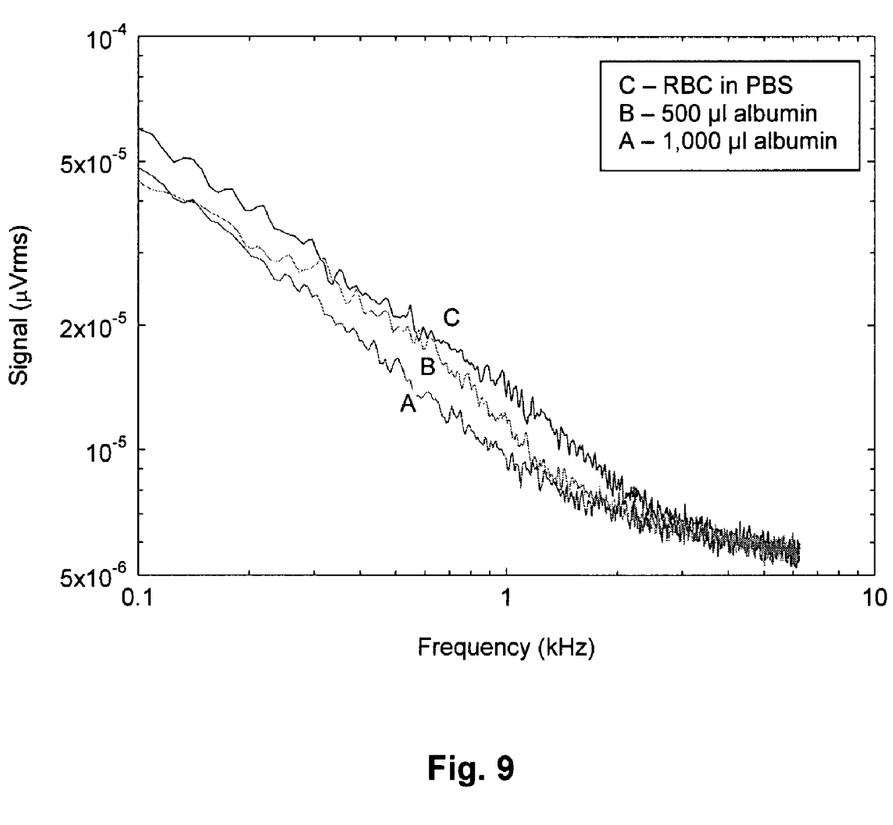
FIG. 9 shows the power spectra of washed red blood cells suspended in PBS and after addition of albumin in the PBS, as described in Example 6.

In the second example, the washed red blood cells were suspended in PBS with a hematocrit of 45%. Albumin was added into the circulation of the red blood cell suspension and the power spectra were recorded after the addition of the protein. FIG. 9 shows the obtained power spectra of blood cells in PBS, and with addition of 500 µl and 1000 µl of albumin, respectively. As shown, addition of albumin to washed erythrocytes increased viscosity in a similar manner to fibrinogen, further indicating the ability of the instant monitor in detecting changes in viscosity induced by proteins. Since these proteins are the major components of plasma, the results of Example 6 have further indicated the utility of the instant optical coagulation monitor in monitoring of coagulation status in vivo, as described more fully hereinafter.

In a further embodiment, the present invention provides a method of determining or monitoring the coagulation status in vivo or in vitro in real time. The method entails the following steps: positioning a sample probe comprising an optical fiber within a circulating blood, transmitting a low-coherence light through the optical fiber into the blood, detecting dynamic, light scatter signals generated by the blood within a coherence volume and received through the optical fiber, analyzing the dynamic light signals in comparison to a predetermined coagulation criterion, and reporting a coagulation status of the blood.

Herein, the term "coagulation status" refers to a blood property relating to coagulation process, such as viscosity of a whole blood, or a change of a blood property relative to time, such as blood viscosity change before, during and after a surgical procedure, or relative to a treatment, such as procoagulant or anticoagulant therapy.

For determination of the coagulation status, the predetermined coagulation criterion can be any one of those parameters described above that can be used as a predetermined clotting criterion, either in the frequency domain or the time domain. For example, using the shape, slope, shear modulus $G(\omega)$ including the storage modulus $G'(\omega)$ and the loss modulus $G''(\omega)$, or other derived parameters of a power spectrum, or the shape or change of the shape or width of the temporal autocorrelation, the predetermined coagulation criterion can be determined with a known value of the parameter from a reference. In one example, the predetermined coagulation criterion is the average value of the loss tangent obtained from the measurement of one or more normal subjects. In another example, the predetermined coagulation criterion is a predetermined amount of change in the width or the shape of the temporal autocorrelation obtained from the measurement of one or more normal subjects.

Moreover, in terms of monitoring, the predetermined coagulation criterion can be one or more of the above described parameters at a reference point of the patient's own blood, for example, the average value of the loss tangent obtained from a patient prior to beginning a surgical procedure, or a clinical treatment. The predetermined coagulation criterion can also be an external reference, for example, a threshold for detection of thrombosis established based on clinical statistics or reference controls.

Furthermore, it should be understood that the predetermined coagulation criterion can also be established based on (i) "instantaneous" measurement of one or more of these parameters, or (ii) the time evolution of one or more of these parameters. "Instantaneous" measurement means one rapid measurement of the power spectrum (typically few seconds), while the time evolution of a parameter is followed for a longer period of time (for example minutes, or tens of minutes). The predetermined coagulation criterion can be determined with a known instantaneous value of the parameter from a reference or can be determined with a known time dependence of the parameter from a reference.

To function as an in vivo diagnostic indicator, one or more of the selected parameters can be illustrated in a manner convenient for the clinical practitioners to use. The predetermined coagulation criterion can be expressed as a threshold or a defined acceptable range. If the selected parameter is below the threshold or within the range, it indicates a normal coagulation status. Alternatively, when the selected parameter is above the threshold or outside the range, the report indicates an abnormal coagulation status. Moreover, since the magnitude of the parameter is quantitative, severity of the patient's condition can also be detected in real time.

As can be appreciated, since the instant method detects the coagulation status in vivo in real time, the patient's response to a drug, either increasing or reducing the risk of clotting, can be monitored and timely reported. As such, important information, such as the rate of response, adverse response if any, and stability of coagulation condition, can be revealed using the instant method. This real time detection capacity has never been achieved previously with existing technologies.

The instant method can also be used to evaluate risk of excessive bleeding prior to a surgical procedure (i.e., pre-surgical screening), monitor bleeding disorders, and can be used for point-of-care testing to monitor a patient's blood coagulation level within therapeutic range, real-time assessment of coagulophaties, or used postoperative to monitor medication effects.

As a specific example, the instant method can be used to monitor the effectiveness of procoagulant or anticoagulant therapies, and particularly to monitor the effect of therapeutic intervention of thrombosis, for example, monitoring a patient under the treatment of a fibrinolytic agent, such as streptokinase. Using the instant optical coagulation monitor, the physician can observe the arrest of viscosity increase due to inhibition of clotting, as well as subsequent viscosity decrease as fibrin oligomers and polymer strands are broken down to smaller, less viscous fibrin degradation products.

The instant multi-mode optical coagulation monitor as illustrated in FIG. 2 and described in Example 2 is currently used for research purpose in a clinic for monitoring patients' coagulation status during surgical procedures (such as a cardiopulmonary bypass). This, for the first time, enables in vivo monitoring of a patient's coagulation status in real time in a clinical environment. Therefore, the present invention provides a significant breakthrough in the early detection of the onset of thrombosis. The resultant early therapeutic intervention can undoubtedly save lives.

The following examples are illustrative of the invention and are in no way to be interpreted as limiting the scope of the invention, as defined in the claims.

EXAMPLE 1

A Single-Mode Optical Coagulation Monitor

An optical coagulation monitor as shown schematically in FIG. 1 was constructed. The major components are described below.

Light source (50) was a superluminiscent diode (SLD) from SUPERLUM (Russia), which had the spectral bandwidth of FWHM 9.0 nm, centered at 676.2 nm. The spectral ripple of the light source was about 0.4% and photodiode current was around 0.954 mA. The SLD was pigtailed with single-mode optic fiber having a fiber inner jacket of 125 µm thick, a fiber core thickness of 8 µm, and FC/APC termination. SLD current and temperature controller (40) was a PILOT-2 from SUPERLUM. Optical isolator (60) was a single-mode optical fiber with a wavelength of 630 nm from Optics for Research (Caldwell, N.J.). The fiber inner jacket was 125 µm thick, and the fiber core thickness was 8 µm. Terminators were FC/PC.

The sample probe (20) comprised a needle (22) with a single-mode optical fiber (80) disposed within. The needle was a 23 gauge (one inch length) Precisionglide from BD (Franklin Lakes, N.J.). A single-mode optical fiber from Thorlabs (Newton, N.J.) was used, which had a wavelength of 630 nm, a fiber inner jacket of 125 µm thick, and a fiber core thickness of 8 µm. The terminators were FC/PC.

Fiber optic splitter (100) was a 2×1 splitter type from Newport (Irvine, Calif.). The fiber type was single-mode fiber with a wavelength of 630 nm. Terminators were FC/PC. The fiber inner jacket thickness was 125 μm, and the fiber core thickness was 8 μm.

The optical detector (70) was a Model 2001 from New Focus (San Jose, Calif.) which was carefully chosen to provide low-noise detection, variable-gain transimpedance amplification of up to 90 dB in 10-dB steps, and two adjustable frequency filters. This particular design allowed selecting the frequency region of interest before additional amplification. The high-pass filter could be adjusted to eliminate residual 60-Hz noise, while the independent low-pass filter could be set to select the bandwidth of interest therefore allowing for efficient and rapid measurements.

A two-channel dynamic light signal analyzer (110), SR785 from Stanford Research Systems (Sunnyvale, Calif.) was used to receive and process the light signals. The analyzer was usually operated in the FFT mode with a base Frequency of 100 Hz and 800 FFT lines. The data viewer, SR785 Data Viewer (Version 1.0) from Stanford Research Systems, was accessed via GPIB to provide further data processing by a personal computer (120).

The blood circulation system (200) included a sample chamber (210), of which inlet 212 and outlet 214 were connected to two opposing ends of a silicone tubing 8060-0020 from Nalgene (Rochester, N.Y.). A Peri-Star 500291 high performance digital peristaltic pump (230) from World Precision Instruments (Sarasota, Fla.) was used. The pump had a fluid flow range of 0.1-80 ml/min. A microprocessor controlled 280 Series water bath from PRECISION (Champaign, Ill.) was used. The temperature was controlled at about 37° C. during the measurement of blood samples.

EXAMPLE 2

A Multi-Mode Optical Coagulation Monitor

A multi-mode optical coagulation monitor (300), as shown schematically in FIG. 2, was constructed.

A single-mode optical fiber (60a), as described in Example 1, was connected to the light source at one end, and was coupled to a multi-mode optical fiber (360) at the opposing end by a coupler (330). The multi-mode optical fiber (60b) was in turn connected to the coupler (110b). Both multi-mode optical fiber (60b) and sample branch (380) were a graded index multimode fiber from Newport (Irvine, Calif.), which operated at a wavelength of 630 nm and had a core thickness of 56 μm. The terminators were FC/PC.

All other components, including light source, SLD current and temperature controller, detector, two-channel dynamic light signal analyzer, personal computer, needle of the sample probe were the same as those described in Example 1. For in vitro measurement, the blood circulation system (200) described in Example 1 can be used.

EXAMPLE 3

Dependence of Power Spectrum on the Hematocrit

The sensitivity of the power spectrum to the hematocrit (Hct) was measured using the multi-mode optical coagulation monitor described in Example 2.

A series of 4 ml reconstituted blood samples with increasing amounts of red blood cells: plasma, Hct of 30%, 35%, 40%, 45%, and 50% were used for the measurement. The tubing and needles were changed for the measurement of each sample, and the optical fiber of the sample probe was cleaned after measurement of each sample. The whole blood collected in acid citrate dextrose (ACD) was supplied by Valley Biomedical Products and Services, Inc. (Winchester, Va.).

The temperature of the blood sample in the sample chamber in the measurements of the samples having Hct of 30% and 35% was at 36.6° C., in the measurements of plasma, and samples having Hct of 40% and 45% was at 35.6° C., and in the measurements of the sample having Hct of 50% was at 37° C., respectively. Each sample was circulated for 5 minutes on the pump at a flow rate of 0.87 ml/min, before the power spectrum was recorded. The light source was operated at 90 mA.

FIG. 4 shows the obtained the power spectra, wherein each curve represents an average of 200 measurements of the power spectrum. As shown, the power spectra of the whole blood samples depended on the hematocrit of the whole blood samples within the hematocrit range tested. However, within the clinical normal hematocrit range, the power spectra were essentially independent of the hematocrit of the blood samples.

Table 1 shows the parameter α obtained by linear fitting of the power spectrum measured at high frequencies, which was indicative of the type of diffusion regime. A strong dependence of α on the hematocrit was observed. This observation indicated a tendency towards normal diffusion ($\alpha=1$), when the hematocrit increased. Since the intensity of the signal obtained for plasma only was much lower than the intensity of the sample having a Hct of 40%, it could be concluded that for the whole blood samples having hematocrit within the clinical normal range, the heterodyne signal was mainly due to the motion of the red blood cells.

TABLE 1

| Hematocrit Level | α |
|---|---|
| 0% (plasma) | 0.14 |
| 30% | 0.2 |
| 35% | 0.45 |
| 40% | 0.75 |
| 45% | 0.82 |
| 50% | 0.76 |

EXAMPLE 4

Measurement of Dynamic Viscosity Change during Thrombosis 3.8 ml of an anti-coagulated whole blood sample was placed into the sample chamber of the multi-mode optical coagulation monitor described in Example 2. The whole blood sample had a hematocrit of 45%. The temperature of the blood was controlled at 35.8° C. during the measurement, and the flow rate of the pump was at 0.87 ml/min. The light source was at 90 mA.

12 μl of thrombin (100 U/ml) was added into the circulating blood in 3 μl increments every 10 minutes over a period of 20 minutes. The thrombin was pre-diluted in a phosphate buffer saline (PBS). The power spectra were recorded after each injection every 30 seconds for 10 minutes, no change of the power spectrum was observed. Then, additional 6 μl of thrombin was added into the blood, and the power spectra were recorded every 30 seconds for 30 minutes. As shown in FIG. 5, changes in viscosity with time were observed. After 22 minutes, a clot formed in front of the optical fiber, and no further change was noted afterwards. FIG. 5 showed the obtained power spectra at 7, 15 and 22 minutes. Each curve was averaged 200 times. FIG. 5 further showed washed red blood cells suspended in PBS, which represented the minimum viscosity obtainable using erythrocytes suspended in a medium with a viscosity close to water. The results showed linear responses across the spectral range.

EXAMPLE 5

Measurement of Blood Clotting Time of Whole Blood Samples

The blood clotting time was measured using the multi-mode optical coagulation monitor described in Example 2 with the blood circulation system described in Example 1. The instrument setting described in Example 4 was used. The two units of whole blood were collected in ACD (from Valley Biomedical Products and Services, Inc.), and had a hematocrit of 45% and 41%, respectively.

3 µl of thrombin per 3 ml of blood were mixed with the blood and directly aspirated at a pump speed of 5-1.2 ml/min into the blood circulation system. The power spectrum was recorded immediately, and every 30 seconds thereafter. Blood coagulation occurred within about 5 to 7 minutes, and an increase in viscosity was observed over time as illustrated in FIG. 6. Sequential increases of the blood viscosity were observed to the point of gel formation due to clotting.

FIG. 6 showed an expanded region of the collected power spectra and a significant decrease in the bandwidth was observed. The actual changes in the viscosity properties were best demonstrated by the changes in the shape of the power spectra. FIG. 7 was a log-log representation of the power spectra. As shown, the slope of the power spectrum changed significantly as the aggregation process evolved.

EXAMPLE 6

Detection of the Effect of Protein Concentration on Blood Viscosity

In the first test, a whole blood collected in ACD (from Valley Biomedical Products and Services, Inc.) was centrifuged, and the plasma fraction was removed and washed (twice to remove all plasma) with PBS. The washed red blood cells were suspended in PBS alone and in PBS solutions that contained 1.3 and 5.5 mg/ml of fibrinogen, respectively. The reconstituted blood cell suspension had a hematocrit of 45%.

Figure 8:
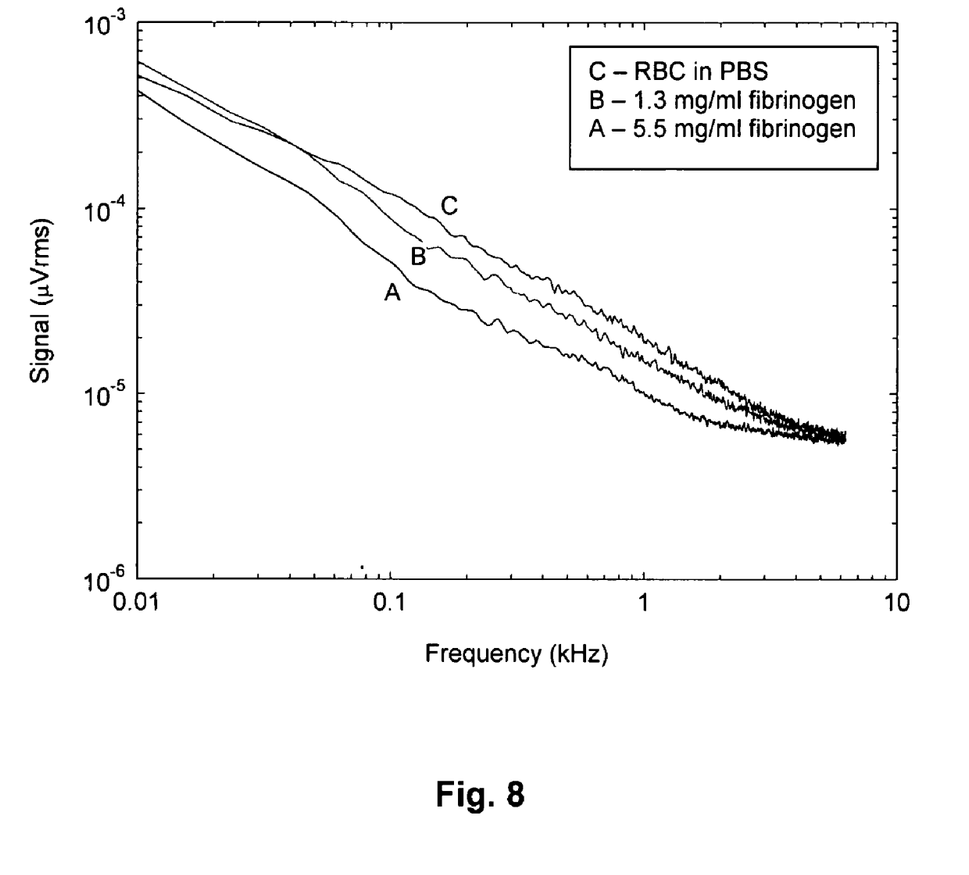
FIG. 8 shows the power spectra of washed red blood cells suspended in PBS and in PBS solutions containing different concentrations of fibrinogen, as described in Example 6.

The power spectra of these three suspensions were obtained using the multi-mode optical coagulation monitor described in Example 2 with the blood circulation system described in Example 1. The temperature was controlled at 36° C. and the flow rate was 0.87 ml/min. The light source was at 90 mA. The obtained power spectra were shown in FIG. 8.

As shown, the viscosity increased with the increase of the concentration of fibrinogen. Furthermore, the increase in viscosity observed at a fibrinogen concentration of 1.3 mg/ml indicated that the instant monitor was sufficiently sensitive to detect small changes in fibrinogen concentration.

In the second test, the washed red blood cells were suspended in PBS with a hematocrit of 45%. The power spectra of the blood cell suspension were obtained using the same device under the same condition, except the temperature was at 36.5° C.

An albumin solution was made at a concentration of 50 mg/ml and was added slowly through an injection port of the silicone tubing placed after the pump and preceding the sample chamber. The power spectra were recorded after the addition of the protein. FIG. 9 showed the obtained power spectra of blood cells in PBS, and with addition of 500 µl and 1000 µl of albumin, respectively. As shown, addition of albumin to washed erythrocytes increased viscosity in a similar manner to fibrinogen, again indicating the ability of the monitor in detecting changes in viscosity induced by proteins.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. An optical coagulation monitor comprising:
   (a) a sample chamber including an inlet and an outlet connected to a circulation path;
   (b) a light source providing a low-coherence light;
   (c) a sample probe disposed within said sample chamber, said sample probe comprising an optical fiber optically connected to said light source for transmitting said low-coherence light into a blood sample contained in said sample chamber;
   (d) an optical detector connected to said sample probe for detecting light signals received from said sample probe;
   (e) a dynamic light signal analyzer connected to said optical detector for analyzing said dynamic light scatter signals in comparison to a predetermined coagulation criterion; and
   (f) a viewer for reporting a coagulation status of said blood.

2. The optical coagulation monitor of claim 1 further comprising a pump connected to said circulation path to circulate said blood sample through said sample chamber.

3. The optical coagulation monitor of claim 1, wherein said optical fiber comprises a single-mode optical fiber or a multi-mode optical fiber.

4. The optical coagulation monitor of claim 1 further comprising an optical coupler connecting to said optical fiber, said light source, and said optical detector for directing said low-coherence light from said light source into said optical fiber and directing said light signals received from said sample probe to said optical detector.

5. The optical coagulation monitor of claim 1, wherein said light source comprises a superluminescent diode, a multiple quantum well light emitting diode, a modelocked $Ti:Al_2O_3$ laser, a laser pumped fluorescent organic dye, or a superfluorescent optical fiber.

6. The optical coagulation monitor of claim 1, wherein said low-coherence light has a coherence length of about 5 µm to about 20 µm.

7. A method of determining or monitoring blood coagulation status comprising:
   (a) positioning a sample probe comprising an optical fiber within a circulating blood;
   (b) transmitting a low-coherence light through said optical fiber into said blood;
   (c) detecting dynamic light scatter signals generated by said blood within a coherence volume and received through said optical fiber;
   (d) analyzing said dynamic light scatter signals in comparison to a predetermined coagulation criterion; and
   (e) reporting a coagulation status of said blood.

8. The method of claim 7, wherein said low-coherence light has a coherence length of about 5 µm to about 20 µm.

9. The method of claim 7, wherein said optical fiber comprises a single-mode optical fiber or a multi-mode optical fiber.

10. The method of claim 7, wherein said detecting said dynamic light scatter signals generates a power spectrum of intensity vs. frequency.

11. The method of claim 10, wherein said predetermined coagulation criterion is a predetermined value or a range of one or more parameters obtained from said power spectrum.

12. The method of claim 11, wherein said predetermined coagulation criterion is a shape or a rate of change in said shape of said power spectrum.

13. The method of claim 11, wherein said predetermined coagulation criterion is a predetermined amount of change of storage modulus G'.

14. The method of claim 11, wherein said predetermined coagulation criterion is a predetermined amount of change of loss modulus G".

15. The method of claim 11, wherein said predetermined coagulation criterion is a predetermined amount of change of loss tangent tanδ.

16. The method of claim 7, wherein said detecting said dynamic light scatter signals of said blood cells generates temporal autocorrelation of said dynamic light scatter signals.

17. The method of claim 16, wherein said predetermined coagulation criterion is a predetermined value or a range of one or more parameters obtained from said temporal autocorrelation.

18. The method of claim 17, wherein said predetermined coagulation criterion is a predetermined amount of change in the shape of said temporal autocorrelation.

19. The method of claim 17, wherein said predetermined coagulation criterion is a predetermined amount of change in the width of said temporal autocorrelation.

20. The method of claim 7, wherein said circulating blood is in vivo.

21. The method of claim 7, wherein said circulating blood is in vitro.

22. The method of claim 7, wherein said monitoring blood coagulation status is in real time.

23. A method of determining blood clotting time comprising:
(a) mixing a coagulation initiator with a blood sample to form a sample mixture;
(b) transmitting a low-coherence light into said sample mixture;
(c) detecting dynamic light scatter signals generated by said sample mixture within a coherence volume;
(d) analyzing said dynamic light scatter signals in comparison to a predetermined clotting criterion; and
(e) reporting said blood clotting time of said blood sample.

24. The method of claim 23, wherein said sample mixture is in a flowing or static condition during said detecting dynamic light scatter signals.

25. The method of claim 23, wherein said low-coherence light has a coherence length of about 5 µm to about 20 µm.

* * * * *